United States Patent
Doerr et al.

(10) Patent No.: US 12,427,327 B2
(45) Date of Patent: Sep. 30, 2025

(54) TEMPORARY IMPLANTABLE LEADLESS PACEMAKER

(71) Applicant: BIOTRONIK SE & Co. KG, Berlin (DE)

(72) Inventors: Thomas Doerr, Berlin (DE); Georg Nollert, Strasslach (DE)

(73) Assignee: BIOTRONIK SE & Co. KG, Berlin (DE)

( * ) Notice: Subject to any disclaimer, the term of this patent is extended or adjusted under 35 U.S.C. 154(b) by 530 days.

(21) Appl. No.: 17/793,233

(22) PCT Filed: Jan. 21, 2021

(86) PCT No.: PCT/EP2021/051305
§ 371 (c)(1),
(2) Date: Jul. 15, 2022

(87) PCT Pub. No.: WO2021/151770
PCT Pub. Date: Aug. 5, 2021

(65) Prior Publication Data
US 2023/0338739 A1    Oct. 26, 2023

(30) Foreign Application Priority Data
Jan. 27, 2020    (EP) .................................... 20153783

(51) Int. Cl.
*A61N 1/375*    (2006.01)
*A61N 1/05*    (2006.01)
(Continued)

(52) U.S. Cl.
CPC .......... *A61N 1/3756* (2013.01); *A61N 1/059* (2013.01); *A61N 1/362* (2013.01); *A61N 1/365* (2013.01);
(Continued)

(58) Field of Classification Search
None
See application file for complete search history.

(56) References Cited

U.S. PATENT DOCUMENTS

2004/0215287 A1* 10/2004 Swoyer .............. A61N 1/36071
607/48
2005/0136385 A1    6/2005 Mann et al.
(Continued)

FOREIGN PATENT DOCUMENTS

| EP | 2818200 A1 | 12/2014 |
|----|----|----|
| EP | 3260167 A1 | 12/2017 |
| EP | 3348306 A1 | 7/2018 |
| WO | 2020018353 A1 | 1/2020 |

OTHER PUBLICATIONS

International Search Report (PCT/ISA/210) and Written Opinion (PCT/ISA/237) mailed on Mar. 31, 2021, by the European Patent Office as the International Searching Authority for International Application No. PCT/EP2021/051305.

*Primary Examiner* — Mallika D Fairchild
(74) *Attorney, Agent, or Firm* — Buchanan, Ingersoll & Rooney PC

(57) ABSTRACT

An implantable leadless pacemaker configured to provide antibradycardia pacing of a human or animal heart, comprising: an electrical energy source, a sensor configured to sense intracardiac potentials of the heart, a pulse generator configured to generate electrical pacing pulses, a control unit for controlling the pulse generator, wherein the control unit is configured to inhibit generation of an electrical pacing pulse when an intracardiac potential is sensed, wherein the control unit is further configured to permanently switch off the pulse generator after passing of a predetermined timespan and/or after a pre-defined event detected by the pacemaker, an electrode pole for electrical stimulation and sensing intracardiac potentials, at least one fastening ele- (Continued)

ment for fastening the pacemaker to heart tissue, wherein the implantable leadless pacemaker is adapted such that a lifetime of the implantable leadless pacemaker is smaller than one year, particularly smaller than one month, particularly smaller than two weeks.

15 Claims, 2 Drawing Sheets

(51) Int. Cl.
    *A61N 1/362*     (2006.01)
    *A61N 1/365*     (2006.01)
    *A61N 1/37*     (2006.01)
    *A61N 1/378*     (2006.01)

(52) U.S. Cl.
    CPC ......... *A61N 1/3702* (2013.01); *A61N 1/3708* (2013.01); *A61N 1/37512* (2017.08); *A61N 1/378* (2013.01)

(56) References Cited

U.S. PATENT DOCUMENTS

| | | | |
|---|---|---|---|
| 2009/0125077 A1* | 5/2009 | Doerr | A61N 1/3684 607/25 |
| 2011/0077708 A1* | 3/2011 | Ostroff | A61N 1/0573 607/2 |
| 2012/0078267 A1* | 3/2012 | Bar-Cohen | A61N 1/362 606/129 |
| 2014/0257324 A1* | 9/2014 | Fain | A61N 1/3756 606/129 |
| 2015/0080855 A1* | 3/2015 | Kassab | A61L 31/148 604/513 |
| 2016/0175601 A1 | 6/2016 | Nabutovsky et al. | |
| 2016/0220828 A1* | 8/2016 | Yan Poon | A61N 1/36139 |
| 2016/0228716 A1* | 8/2016 | Schmidt | A61N 1/362 |
| 2016/0367822 A1* | 12/2016 | Parramon | A61N 1/3787 |
| 2017/0202467 A1* | 7/2017 | Zitnik | A61N 1/3787 |
| 2018/0207427 A1* | 7/2018 | Webb | A61N 1/3756 |
| 2018/0264274 A1* | 9/2018 | Haasl | A61N 1/059 |
| 2019/0083800 A1* | 3/2019 | Yang | A61N 1/0573 |
| 2020/0016418 A1 | 1/2020 | Makharinsky | |

* cited by examiner

TEMPORARY IMPLANTABLE LEADLESS PACEMAKER

CROSS-REFERENCE TO RELATED APPLICATIONS

This application is the United States National Phase under 35 U.S.C. § 371 of PCT International Patent Application No. PCT/EP2021/051305, filed on Jan. 21, 2021, which claims the benefit of European Patent Application No. 20153783.4, filed on Jan. 27, 2020, the disclosures of which are hereby incorporated by reference herein in their entireties.

TECHNICAL FIELD

The present invention relates to an implantable leadless pacemaker for temporary stimulation.

BACKGROUND

A temporary pacemaker to treat a bradycardia is used if a permanent pacemaker is either not necessary or is not immediately available.

Such a temporary stimulation is usually performed with a temporary electrode lead connected to an external stimulator.

U.S. Publication No. 2014/0257324 discloses a method and a system for removing, from an implant chamber of a heart, a leadless implantable medical device (LIMD) having a distal end and a proximal end. The distal end is configured to be actively secured to tissue in the implant chamber of the heart. The proximal end is configured to be coupled to a distal end of an indwelling retrieval mechanism (IRM). The IRM extends from the heart along a vessel, the IRM having a proximal end configured to be anchored at a temporary anchor site. The method comprises detaching the IRM from the anchor site, loading a retrieval tool over the proximal end of the IRM and along the body of the IRM. The retrieval tool has a lumen therein that receives the IRM as the retrieval tool re-enters the vessel, thereby allowing the retrieval tool to engage the LIMD.

Disadvantages of temporary stimulation using an electrode lead and an external cardiac pacemaker are the need to hospitalize and monitor the patient for the time of temporary stimulation and the associated costs and limitations for the patient.

Further disadvantages of temporary stimulation by electrode lead and external cardiac pacemaker are complications, especially the risk of probe dislocation, endocarditis and incorrect operation and manipulation of the external pacemaker or electrode by the patient or hospital staff.

The present disclosure is directed toward overcoming one or more of the above-mentioned problems, though not necessarily limited to embodiments that do.

SUMMARY

Based on the above, it is an objective of the present invention, to offer reliable temporary stimulation of patients without the need for hospitalization and at the same time significantly reducing complications of temporary stimulation.

To this end, claim 1 discloses an implantable leadless pacemaker configured to provide temporary antibradycardia pacing of a patient's heart, comprising:
an electrical energy source,
a sensor configured to sense an intracardiac potential (particularly the intracardiac QRS potential) of the heart,
a pulse generator configured to generate electrical pacing pulses,
a control unit for controlling the pulse generator, wherein the control unit is configured to inhibit generation of an electrical pacing pulse when an intracardiac potential is sensed, wherein the control unit is further configured to permanently switch off the pulse generator after passing of a predetermined timespan and/or after a pre-defined event detected by the pacemaker,
an electrode pole for electrical stimulation and sensing intracardiac potentials,
at least one fastening element for fastening the pacemaker to heart tissue, and wherein
the implantable leadless pacemaker is adapted such that a lifetime of the implantable leadless pacemaker is smaller than one year, particularly smaller than one month, particularly smaller than two weeks.

Particularly, lifetime means that the capability of the pacemaker to deliver electrical stimulation pulses is limited in time. Particularly, after passing of the lifetime, the pacemaker is no longer able to deliver electrical stimulation pulses, particularly due to depletion of the electrical energy source.

Said pre-defined event detected by the pacemaker is, according to embodiments of the present invention, at least one of the following events:
interrogation with an external programmer device during a follow-up visit,
magnetic or electric alternating or permanent field, and/or electric pulse originating from a different (cardiac) implant.

The present invention solves the task of offering reliable temporary stimulation of patients over several days to weeks without the need for hospitalization and at the same time significantly reducing complications of temporary stimulation and eliminating unwanted manipulations of the temporary pacemaker.

In an embodiment, said electrode pole (for example, a cathode) is arranged on a face side of an elongated housing of the pacemaker, which housing encapsulates the electrical energy source, the pulse generator, the sensor, and the control unit. In other words, the pacemaker does not comprise a flexible electrode lead containing the pole(s) for sensing/stimulation connected to the housing.

Particularly, the pacemaker comprises a further electrode pole (for example, an anode) for bipolar pacing and sensing. The further electrode pole can be arranged on a lateral circumferential surface of the housing.

Particularly, according to an embodiment, when being fully charged, the electrical energy source comprises a capacity in the range from 0.1 mAh to 30 mAh.

Particularly, applications for the implantable leadless pacemaker according to the present invention are all indications for temporary stimulation, for example:
after a TAVI implantation,
after ablation therapy (PVI) with temporary AV blockade,
bridging with defibrillator vest and temporary stimulation,
*Borrelia* Myocarditis,
after posterior myocardial infarction with occlusion of the right coronary artery,
in AV block under one of: antidepressants, antirheumatic drugs, beta-blockers (generally: *medica mentenin* induced) for the time of the drug washout,
after cardiosurgical interventions.

Particularly, in an embodiment, the pacemaker is configured to operate in SSI mode, i.e., the pacemaker/control unit inhibits pacing (i.e., the generation of electrical stimulation pulses) when intracardiac potentials are sensed. Particularly, the pacemaker outputs electrical stimulation pulses if no event is sensed within one of the intervals corresponding to a selected frequency of the pacemaker.

Further, according to an embodiment of the implantable leadless pacemaker, the electrical energy source is a solid state battery. Such a battery comprises, for example, an electrolyte in a solid state, for example, a solid ceramic electrolyte, and particularly no liquid electrolyte at all.

Further, according to an embodiment of the implantable leadless pacemaker, a volume of the implantable leadless pacemaker is less than 0.5 cm$^3$, preferably less than 0.25 cm$^3$, preferably less than 0.15 cm$^3$, preferably less than 0.1 cm$^3$.

Further, according to an embodiment of the implantable leadless pacemaker, the implantable leadless pacemaker is configured to be implanted into the right ventricle by means of a catheter device.

Furthermore, according to an embodiment, the pacemaker is configured to be fastened to the heart in such a fashion that the pacemaker is explantable after the planned duration of use.

Furthermore, an aspect of the present invention relates to a system comprising an implantable leadless pacemaker and a catheter device configured to implant and particularly explant the implantable leadless pacemaker.

Furthermore, according to an embodiment of the implantable leadless pacemaker, the implantable leadless pacemaker is configured to be activated via the catheter device. According to an alternative embodiment, the implantable leadless pacemaker is configured to be activated before implantation.

Further, according to an embodiment of the implantable leadless pacemaker, the electrical energy source is a rechargeable battery (for example, a rechargeable solid state battery, see above), particularly with charge/charge maintenance before implantation/packaging.

Further, according to an embodiment of the implantable leadless pacemaker, the leadless pacemaker is configured to be programed before implantation. According to an alternative embodiment, the implantable leadless pacemaker is configured to be programmed after implantation via the catheter device.

Further, according to an embodiment of the implantable leadless pacemaker, at least the electrical energy source, the sensor, the pulse generator and the control unit are one of: embedded in a liquid crystal polymer, coated with parylene, encapsulated in a silicone, encapsulated in an epoxy resin, encapsulated in a metallic housing, encapsulated in a ceramic housing.

Further, according to an embodiment of the implantable leadless pacemaker, the implantable leadless pacemaker comprises an elongated housing carrying the electrical energy source, the sensor, the pulse generator, the control unit and the electrode pole(s), wherein particularly the housing is flexible or comprises a flexible portion (e.g., for carrying an electrode pole).

Furthermore, according to an embodiment of the system (see above), the catheter device is configured such that electrical measurements in the heart (for example, at least one of: mapping, sensing amplitudes, measuring impedances) can be carried out via the catheter device, the pacemaker connected thereto, and an external device.

Furthermore, according to an embodiment of the system, the catheter device is configured such that electrical stimulations in the heart can be carried out via the catheter device, the implantable leadless pacemaker connected thereto, and an external device (threshold measurement, rapid pacing for Trans-Aortic Valve (TAVI) implantations, Anti-Tachycardia Pacing (ATP), etc.).

Furthermore, according to an embodiment of the implantable leadless pacemaker, the leadless pacemaker is configured to adapt a stimulation energy to a current stimulation threshold.

Further, according to an embodiment of the implantable leadless pacemaker, the implantable leadless pacemaker is configured to detect another implanted pacemaker and to automatically switch off delivering electrical stimulation pulses in case it detects another implanted pacemaker is detected.

Further, according to an embodiment of the implantable leadless pacemaker, the implantable leadless pacemaker is configured to operate in VVI mode. In this case, the implantable leadless pacemaker is configured to be implanted into a ventricle of the heart. Particularly, VVI mode means ventricular demand pacing, i.e., the ventricle is paced, sensed, and the control unit inhibits output of an electrical stimulation pulse in response to a sensed ventricular event.

Further, according to an embodiment of the implantable leadless pacemaker, the implantable leadless pacemaker comprises a stimulation frequency in the range from 40 bpm to 65 bpm (wherein bpm denotes beats per minute).

Further, according to an embodiment of the implantable leadless pacemaker, the implantable leadless pacemaker comprises a frequency hysteresis function.

In this context, frequency hysteresis is understood as a function of the pacemaker not to intervene immediately as soon as the intrinsic heart rhythm falls below the pacemaker's pacing rate. Instead, the pacemaker is configured to intervene when the intrinsic heart rate has fallen below said pacemaker's pacing rate by a certain tolerance. For example, the pacemaker can be configured to intervene at an intrinsic heart rate of less than 60 bpm, but then stimulates with 70 bpm. The frequency hysteresis function favors the heart's intrinsic rhythm rather than pacemaker induced cardiac rhythm.

Furthermore, according to an embodiment of the implantable leadless pacemaker, the implantable leadless pacemaker is MRI-compatible.

MRI compatibility is achieved by appropriate hardware and software design of the pacemaker. Implantable leadless pacemakers are very short and have no elongated electrode line, so that the high frequency fields of the MRI machine would induce no significant inductive coupling to the implant.

According to yet another embodiment of the implantable leadless pacemaker, the implantable leadless pacemaker comprises a steroid-releasing reservoir to avoid increases in stimulus thresholds after implantation.

A further aspect of the present invention relates to a method for treating patients in need of a temporary pacemaker and, in particular, a method for antibradycardia stimulation of the human or animal heart, wherein the method comprises the steps of: implanting a leadless pacemaker for temporary or permanent placement in the heart; delivering demand-driven electrical stimulation to the heart for a predetermined period of time in the range from one day to three months; and permanently deactivating delivery of electrical stimulation to the heart after a pre-determined timespan has passed and/or after a pre-determined event is detected by the implanted leadless pacemaker.

The basic idea of this aspect of the present invention is to avoid the need to hospitalize and monitor the patient for the time of temporary stimulation and the associated costs and limitations for the patient which comes with the use of electrode leads and an external pacemaker. A leadless pacemaker is used instead. Such a leadless pacemaker could be easily implanted by the use of a correspondingly configured catheter. The patients could leave the hospital at the same or the next day. The use of a small leadless pacemaker as described above further contributes to a simplified and easier catheter-based implantation.

According to an embodiment, the predetermined period of time for delivering demand-driven electrical stimulation to the heart is in a range from one day to four weeks, or from one day to three weeks, or from one day to two weeks, or from one day to one week.

According to an embodiment, the method further comprises explanting the implantable leadless pacemaker.

According to a further embodiment, the method further comprises activating and/or programming the implantable leadless pacemaker before or during implantation.

According to a further embodiment of the method, the method further comprises the step of charging or trickle charging the electrical energy source prior to implantation.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

In the following, embodiments of the present invention as well as further features and advantages of the present invention shall be described with reference to the Figures, wherein.

DETAILED DESCRIPTION

Figure 2A:
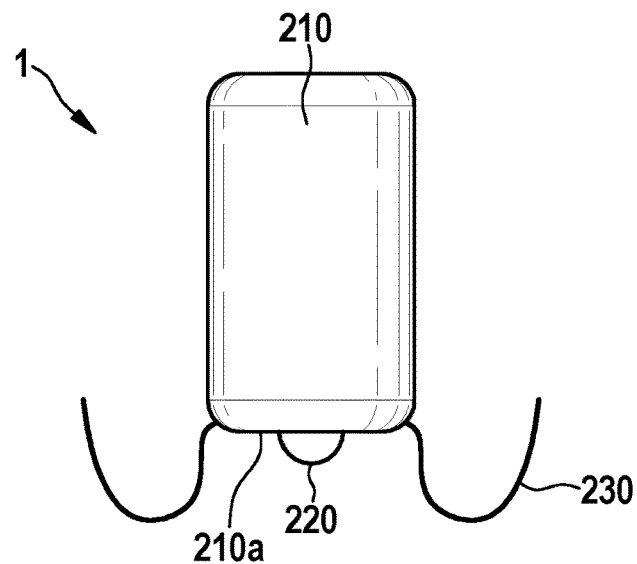
FIG. 2A shows a schematic illustration of an embodiment of an implantable leadless pacemaker according to the present invention.
Figure 2B:
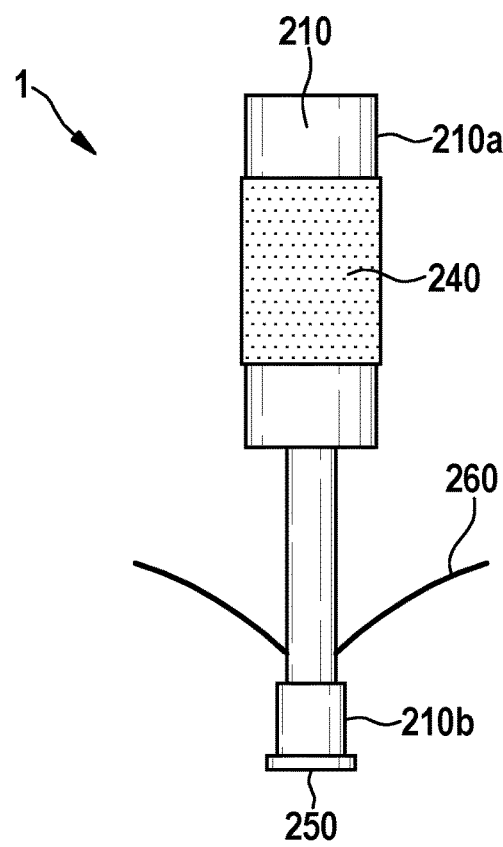
FIG. 2B shows a view of a further embodiment of an implantable leadless pacemaker according to the present invention.

FIGS. 2A and 2B show embodiments of an implantable leadless pacemaker 1 according to the present invention. Such a pacemaker 1 preferably comprises an electrical energy source 120, a sensor 140 to sense intracardiac potentials of the heart, a pulse generator 140 to generate electrical pacing pulses, and a control unit 140 for controlling the pulse generator, wherein the control unit is configured to inhibit generation of an electrical pacing pulse when an intracardiac potential is sensed, wherein the control unit is further configured to permanently switch off the pulse generator after passing of a predetermined timespan and/or after a pre-defined event detected by the pacemaker. Furthermore, the pacemaker 1 comprises an electrode pole 220, 250 for electrical stimulation and sensing intracardiac potentials and at least one fastening element 230, 260 for fastening the pacemaker 1 to heart tissue. According to the present invention, the implantable leadless pacemaker is adapted such that a lifetime of the implantable leadless pacemaker is smaller than one year, particularly smaller than one month, particularly smaller than two weeks. This allows minimizing the dimension of the pacemaker 1 in an advantageous fashion, which in turn minimizes risks related to implantation of the pacemaker 1.

Figure 1A:
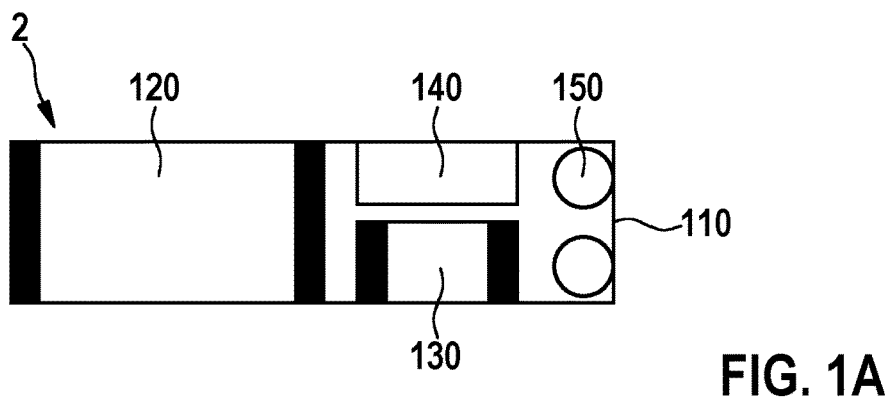
FIG. 1A shows a schematic top view onto an electronic module of an implantable leadless pacemaker according to the present invention.
Figure 1B:
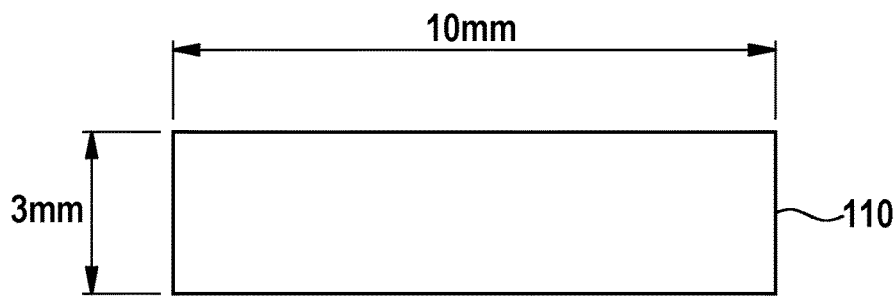
FIG. 1B shows exemplary dimensions of a substrate of the electronic module (top view)
Figure 1C:
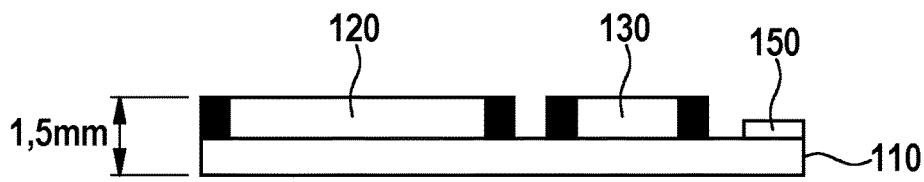
FIG. 1C shows a side view of the electronic module shown in FIG. 1.

FIG. 1A shows an embodiment of an electronic module 2 of an implantable leadless pacemaker 1 according to the present invention. The module 2 is arranged on a substrate 110 and carries an electrical energy source in form of a rechargeable solid state battery 120 (for example, a TDK CeraCharge™~4.5×3 mm, 1.4 V, 100 µAh), a capacitor 130 (for storing the electrical energy of the successive stimulation pulse, for example, ~3×1.5×1 mm), an integrated circuit 140 (for example, a Mixed Mode IC, e.g., 55 nm 3 mm$^2$) and two pads 150 connected to perception and stimulation electrode poles. The integrated circuit 140 forms said sensor, said pulse generator, and the control unit for controlling the pulse generator. Particularly, the dimensions of the module are shown in FIG. 1B and FIG. 1C. The volume of the modules would be, e.g., 0.05 cm$^3$.

Figure 1D:
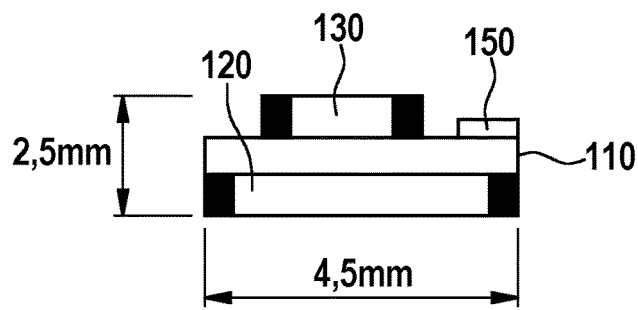
FIG. 1D shows a side view of an alternative embodiment of the electronic module.

FIG. 1D shows an alternative configuration in form of a double-sided substrate assembly which would comprise an even smaller volume of 0.034 cm$^3$. Here, the solid state battery can be arranged on one side of the substrate 110, while the capacitor 130 and the pads 150 can be arranged on the other side of the substrate 110.

The dimensions stated in FIGS. 1A to 1D are examples.

In order to realize such a small design, the functional scope of the implant is preferably reduced to the following functions, for example:

SSI (AAI or VVI) mode,
a basic frequency in the range from 40 bpm to 65 bpm),
a frequency hysteresis (for a better assessment of the intrinsic rhythm in the surface ECG),
a galvanic activation of the implant via the electrode poles,
automatic deactivation of the implant 1 after a fixed time (for example, 14 days),
power and battery charge management (via electrode poles), The battery capacity selected in the example (100 µA@1.4V) would allow a runtime at 100% stimulation with 60 bpm, 1.0V@0.4 ms, 500 Ohm of ~2 days. An extension of the running time to 14 days would increase the volume of the electronic module by 0.09 cm$^3$. Announced Solid State battery technologies partly have a double energy seal, so that the running time of an, e.g., 0.12 cm$^3$ large electronic module can amount to 24 days.

FIG. 2A shows an embodiment of an implantable leadless pacemaker 1, comprising a housing 210, a stimulation electrode pole 220 (arranged on a face side 210a of the elongated housing 210) and at least one fastening element (for example, in a form of a tine). The housing 210 can be made of a metal, a metal oxide, a silicone, an LCP, an epoxy resin or a ceramic material. A housing volume of 0.5 cm$^3$-0.1 cm$^3$ can be achieved by analogy with the well-known iLPs (shorter running time ~5%, smaller functional scope). Preferably, the pacemaker 1 comprises the above-described electronic module 2 that is enclosed by the housing. The at least one fastening element 230 is arranged on said face side of the housing so that the electrode pole 220 is in contact with heart tissue once the pacemaker 1 is anchored to the heart using the at least one fastening element 230.

FIG. 2B shows an alternative embodiment of an implantable leadless pacemaker according to the present invention. Here, the electronic module 2 is preferably integrated beneath a ring electrode pole 240 into a portion 210*a* of a housing 210 of the pacemaker, which housing portion 210*a* is formed out of, e.g., silicone or PU and is preferably flexibly connected to an electrode head 210*b* (here passive) of the housing 210, which head 210*b* comprises fixing tines 260 as fastening elements and an electrode pole 250 on the tip of the electrode head 210*b*. Here, as an example, the pacemaker 1 can comprise a length of 10 mm, a diameter of 5 mm, and a volume of 0.2 cm³.

The inventive solution offers the potential to serve all temporary pacemaker applications and thus eliminates the disadvantages of hospitalization and complications of current temporary stimulation.

Due to the very small range of functions required, such a stimulation system can be manufactured with low costs and thus contributes to considerable cost savings in passive stimulation. Furthermore, the system is particularly MRI-capable, which allows the status of a *Borrelia* myocarditis, for example, to be diagnosed in the MRI.

In view of all the foregoing disclosure, the present invention also provides for the following consecutively numbered embodiments:

1. An implantable leadless pacemaker (1) configured to provide antibradycardia pacing of a human or animal heart, comprising:
   an electrical energy source (120),
   a sensor (140) configured to sense intracardiac potentials of the heart,
   a pulse generator (140) configured to generate electrical pacing pulses,
   a control unit (140) for controlling the pulse generator, wherein the control unit is configured to inhibit generation of an electrical pacing pulse when an intracardiac potential is sensed, wherein the control unit is further configured to permanently switch off the pulse generator after passing of a predetermined timespan and/or after a pre-defined event detected by the pacemaker (1),
   an electrode pole (220, 250) for electrical stimulation and sensing intracardiac potentials,
   at least one fastening element (230, 260) for fastening the pacemaker (1) to heart tissue, wherein
   the implantable leadless pacemaker (1) is adapted such that a lifetime of the implantable leadless pacemaker (1) is smaller than one year, particularly smaller than one month, particularly smaller than two weeks.
2. The implantable leadless pacemaker according to embodiment 1, wherein the electrical energy source (120) is a solid state battery.
3. The implantable leadless pacemaker according to embodiment 1 or 2, wherein the electrical energy source comprises a capacity in the range from 0.1 mAh to 30 mAh.
4. The implantable leadless pacemaker according to embodiment 1 to 3, wherein a volume of the implantable leadless pacemaker (1) is smaller than 0.5 cm³, preferably smaller than 0.25 cm³, preferably smaller than 0.15 cm³, preferably smaller than 0.1 cm³.
5. The implantable leadless pacemaker according to one of the preceding embodiments, wherein at least the electrical energy source (120), the sensor (140), the pulse generator (140) and the control unit (140) are one of: embedded in a liquid crystal polymer, coated with parylene, encapsulated in a silicone, encapsulated in an epoxy resin, encapsulated in a metallic housing, encapsulated in a ceramic housing.
6. The implantable leadless pacemaker according to one of the preceding embodiments, wherein the implantable leadless pacemaker (1) comprises an elongated housing (210) carrying the electrical energy source (120), the sensor (140), the pulse generator (140), the control unit (140) and the electrode pole (220, 250), wherein particularly the housing is flexible or comprises a flexible portion.
7. The implantable leadless pacemaker according to one of the preceding claims, wherein the implantable leadless pacemaker (1) is configured to detect another implanted pacemaker and to automatically switch off delivering electrical stimulation pulses in case another implanted pacemaker is detected.
8. The implantable leadless pacemaker according to one of the preceding embodiments, wherein the implantable leadless pacemaker (1) is configured to operate in VVI mode.
9. The implantable leadless pacemaker according to one of the preceding embodiments, wherein the implantable leadless pacemaker (1) comprises a stimulation frequency in the range from 40 bpm to 55 bpm.
10. The implantable leadless pacemaker according to one of the preceding embodiments, wherein the implantable leadless pacemaker (1) comprises a frequency hysteresis function.
11. The implantable leadless pacemaker according to one of the preceding embodiments, wherein the implantable leadless pacemaker (1) is MRI-compatible.
12. The implantable leadless pacemaker according to one of the preceding embodiments, wherein the implantable leadless pacemaker (1) comprises a steroid-releasing reservoir to avoid increases in stimulus thresholds after implantation.
13. A method for anti-bradycardia stimulation of the human or animal heart, wherein the method comprises the steps of: implanting a leadless pacemaker (1) for temporary or permanent placement in the heart; delivering demand-driven electrical stimulation to the heart using the pacemaker (1) for a predetermined period of time in the range from one day to three months; and permanently deactivating delivery of electrical stimulation to the heart via the pacemaker (1) after a predetermined timespan has passed and/or after a predetermined event is detected by the implanted leadless pacemaker.
14. The method according to embodiment 13, wherein the method further comprises explanting the implantable leadless pacemaker (1).
15. The method according to embodiments 13 or 14, wherein the method further comprising activating and/or programming the implantable leadless pacemaker (1) before or during implantation.
16. The method according to one of the embodiments 13-15, wherein the implantable leadless pacemaker is the implantable leadless pacemaker (1) according to one of the embodiments 1 to 12.
17. A method for treating a patient in temporary need for a pacemaker comprising the catheter-based implantation of an implantable leadless pacemaker (1).

18. The method according to embodiment 17, wherein an anti-bradycardia stimulation according to any of the embodiments 13-16 is delivered.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable leadless pacemaker configured to provide antibradycardia pacing of a human or animal heart, comprising:
   an electrical energy source,
   a sensor configured to sense intracardiac potentials of the heart,
   a pulse generator configured to generate electrical pacing pulses,
   a control unit for controlling the pulse generator, wherein the control unit is configured to inhibit generation of an electrical pacing pulse when an intracardiac potential is sensed, wherein the control unit is further configured to permanently switch off the pulse generator after passing of a predetermined timespan and/or after a pre-defined event detected by the pacemaker,
   an electrode pole for electrical stimulation and sensing intracardiac potentials,
   at least one fastening element for fastening the pacemaker to heart tissue.

2. The implantable leadless pacemaker according to claim 1, wherein the electrical energy source is a solid state battery.

3. The implantable leadless pacemaker according to claim 1, wherein the electrical energy source comprises a capacity in the range from 0.1 mAh to 30 mAh.

4. The implantable leadless pacemaker according to claim 1, wherein a volume of the implantable leadless pacemaker is smaller than 0.5 cm$^3$.

5. The implantable leadless pacemaker according to claim 1, wherein at least the electrical energy source, the sensor, the pulse generator and the control unit are one of: embedded in a liquid crystal polymer, coated with parylene, encapsulated in a silicone, encapsulated in an epoxy resin, encapsulated in a metallic housing, encapsulated in a ceramic housing.

6. The implantable leadless pacemaker according to claim 1, wherein the implantable leadless pacemaker comprises an elongated housing carrying the electrical energy source, the sensor, the pulse generator, the control unit and the electrode pole, wherein the housing is flexible or comprises a flexible portion.

7. The implantable leadless pacemaker according to claim 1, wherein the implantable leadless pacemaker is configured to detect another implanted pacemaker and to automatically switch off delivering electrical stimulation pulses in case another implanted pacemaker is detected.

8. The implantable leadless pacemaker according to claim 1, wherein the implantable leadless pacemaker is configured to operate in VVI mode.

9. The implantable leadless pacemaker according to claim 1, wherein the implantable leadless pacemaker comprises a stimulation frequency in the range from 40 bpm to 55 bpm.

10. The implantable leadless pacemaker according to claim 1, wherein the implantable leadless pacemaker comprises a frequency hysteresis function.

11. The implantable leadless pacemaker according to claim 1, wherein the implantable leadless pacemaker is MRI-compatible.

12. The implantable leadless pacemaker according to claim 1, wherein the implantable leadless pacemaker comprises a steroid-releasing reservoir to avoid increases in stimulus thresholds after implantation.

13. A method for anti-bradycardia stimulation of the human or animal heart, wherein the method comprises the steps of: implanting a leadless pacemaker for temporary or permanent placement in the heart; delivering demand-driven electrical stimulation to the heart; and permanently deactivating delivery of electrical stimulation to the heart via the pacemaker after a pre-determined timespan has passed and/or after a pre-determined event is detected by the implanted leadless pacemaker.

14. The method according to claim 13, wherein the method further comprises explanting the implantable leadless pacemaker.

15. The method according to claim 13, wherein the method further comprising activating and/or programming the implantable leadless pacemaker before or during implantation.

* * * * *